United States Patent [19]

Warriner

[11] Plant 4,331

[45] Nov. 7, 1978

[54] ROSE PLANT

[75] Inventor: William A. Warriner, Tustin, Calif.

[73] Assignee: Jackson & Perkins Co., Medford, Oreg.

[21] Appl. No.: 852,964

[22] Filed: Nov. 18, 1977

[51] Int. Cl.[2] ..... A01H 5/00
[52] U.S. Cl. ..... Plt./26
[58] Field of Search ..... Plt./26

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

A new and distinct cultivar of rose plant of the Floribunda class, heavily branched and compact plant, having a novel flower color of Wilson's Coral Pink, with little fragrance.

1 Drawing Figure

The present invention relates to a new and distinct cultivar of rose plant of the Floribunda class which was originated by me by crossing the cultivar Bridal Pink, U.S. Plant Pat. No. 2,851 with pollen of the cultivar Matador, U.S. Plant Pat. No. 3,229.

The primary objective of this breeding was to produce a cultivar of the Floribunda class which was to grow in a dense, compact manner, similar to both parents, and bear blooms of a color not so pale as Bridal Pink and with more petal substance than Bridal Pink. This objective was substantially achieved along with other desirable improvements as evidenced by the following unique combination of characteristics which are outstanding in this new cultivar and which distinguish it from its parents as well as from all other cultivars of which I am aware:

1. A heavily branched, compact plant reaching a normal height of 3 to 4 feet at Irvine, Calif.
2. Unusually large foliage which very commonly contains seven leaflets per leaf.
3. A novel flower color in this class of Wilson's Coral Pink.
4. An attractive, slowly opening flower form which is maintained well by the heavy petal substance.
5. Very little fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Bridal Pink, U.S. Plant Pat. No. 2,851.

*Pollen parent.*—Matador, U.S. Plant Pat. No. 3,229.

Classification:

*Botanical.*—Rosa Hybrid.

*Commercial.*—Floribunda.

FLOWER

Observations made from specimens grown at Irvine, Calif., in August of 1977.

Blooming habit: Continuous.

Bud:

*Size.*—$\frac{3}{4}''$ to 1″ when petals start to unfurl.

*Form.*—Blunt top.

*Color.*—When sepals first divide, near Begonia (619/1) at distal portion, gradually lighter toward base to a large area of color near Straw Yellow (604/3); when half blown, upper side of petals near Coral Pink (0619); lower side of petals near Coral Pink (0619/1).

*Sepals.*—Color: Outer surface Scheele's Green (860) with numerous small stipitate glands; inner surface, Scheele's Green (860/3) with a thin, white tomentum. Three appendaged sepals heavily appendaged. Two unappendaged sepals hairy edged.

*Receptacle.*—Color: Scheele's Green (860). Shape: Funnel. Size: Large, long. Surface: Smooth.

*Peduncle.*—Length: Medium. Surface: Prickly. Color: Medium green. Strength: Stiff, erect.

*Opening.*—Petals fold out, recurving slightly. When fully open, outer petals pointed.

Bloom:

*Size.*—Medium. Average open size 3″ to $3\frac{1}{2}''$.

*Borne.*—Singly and in flat clusters.

*Stems.*—Medium to short.

*Form.*—When first open, high centered. Permancence: Flattens, with petal edges slightly curled.

*Petalage.*—Number of petals under normal conditions: 25 to 35.

*Color.*—Center of flower: Upper side of petals: Coral Pink (0619/1). Reverse side of petals: Near Coral Pink (0619/2). Base of petals: Indistinct area of Mimosa Yellow (602/1), grading lighter toward center of petal, blending with Coral Pink (0619/3). General tonality from a distance: Coral Pink (0619/1).

*Variegations.*—None.

*Discoloration.*—General tonality at end of first day, no change; third day, lightens generally after third day to Venetian Pink (420/3).

*Fragrance.*—Slight.

Petals:

*Texture.*—Thick.
*Shape.*—Round.
*Form.*—Tips slightly recurved and edges slightly quilled.
*Arrangement.*—Imbricated. Petaloids in center, few.
*Persistence.*—Drop off cleanly.
*Lastingness.*—On the plant, very long. As cut flower, very long.

Reproductive parts:
*Stamens, anthers.*—Small, many. Color, yellow. Arrangement, regular around styles.
*Filaments.*—Color: Very light yellow.
*Pollen.*—Gold yellow.
*Styles.*—Color: Geranium Lake (20).
*Stigmas.*—Color: Light yellow.

PLANT

Form: Bush.
Growth: Very vigorous, upright, branching.
Foliage: Number of leaflets on normal mid-stem leaves five or seven.
*Size.*—Very large.
*Quantity.*—Normal.
*Color.*—New foliage: Garnet Brown (00918). Old foliage: Near Parsley Green (00962).

Leaflets:
*Shape.*—Broad oval, pointed.
*Texture.*—Leathery.

*Edge.*—Serrated
*Serrations.*—Single, small.
*Petiole.*—Rachis: Color, reddish. Underside: Prickles.
*Stipules.*—Long, bearded.
*Disease resistance.*—Normally resistant to mildew under normal growing conditions at Irvine, Calif.

Wood:
*New wood.*—Color: Dark green. Bark: Smooth.
*Old wood.*—Color: Green Bark: Smooth.

Prickles:
*Quantity.*—On main stalks from base, many. On laterals from stalk, many.
*Form.*—Narrow base, long, hooked slightly downward.
*Color when young.*—Brown.
*Position.*—Irregular.

Small prickles:
*Quantity.*—On main stalks, few. On laterals, few.
*Color.*—Brown.

I claim:

1. A new and distinct cultivar of rose plant of the Floribunda class, substantially as herein shown and described, characterized particularly as to novelty by the unique combination of its uniform, compact, dense plant, large foliage, well-formed, coral pink blooms of heavy substance.

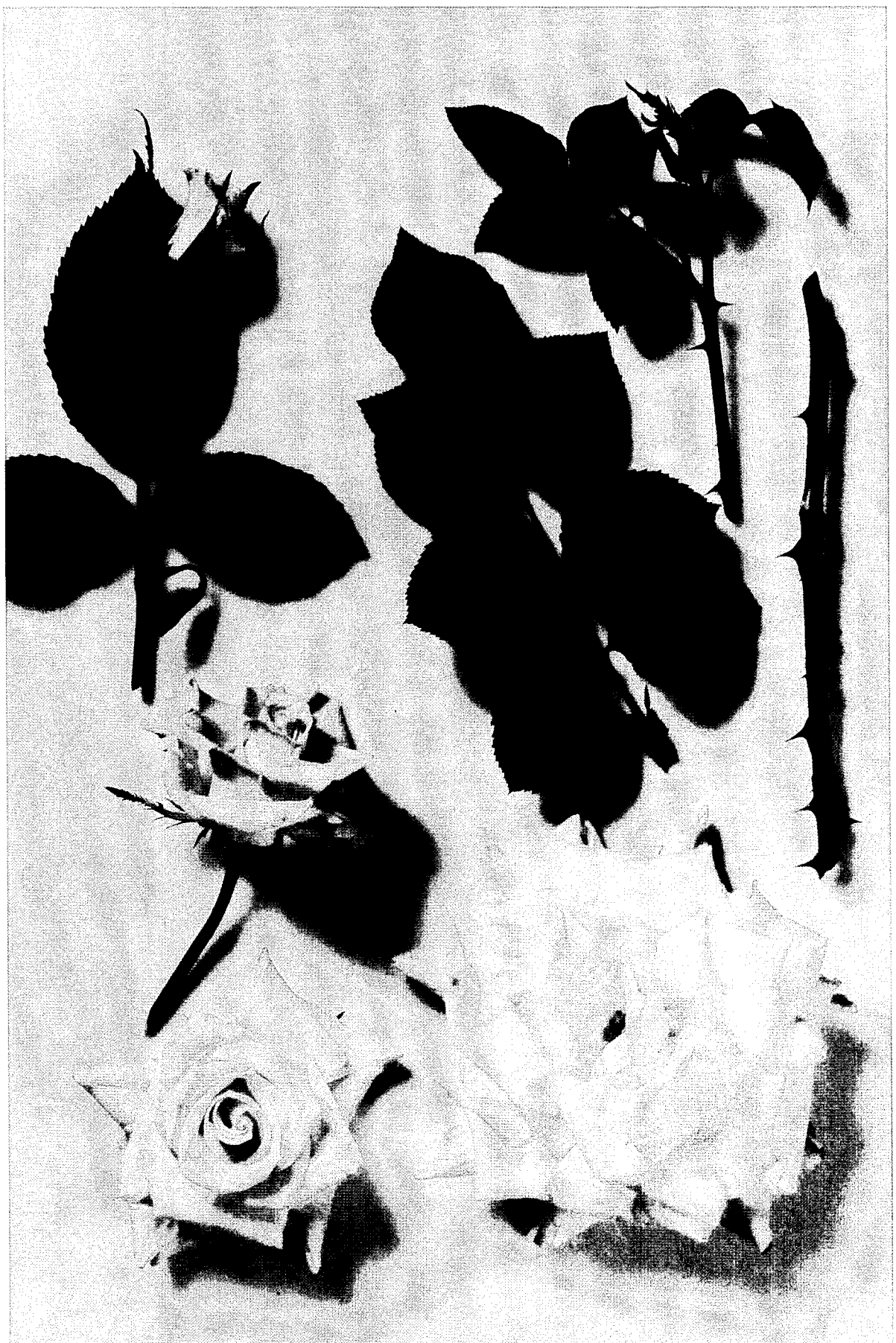

* * * * *